United States Patent [19]

Wickramasinghe

[11] 4,378,699
[45] Apr. 5, 1983

[54] SCANNING ACOUSTIC MICROSCOPE

[75] Inventor: Hemantha K. Wickramasinghe, London, England

[73] Assignee: National Research Development Corporation, London, England

[21] Appl. No.: 229,576

[22] PCT Filed: May 15, 1980

[86] PCT No.: PCT/GB80/00089
§ 371 Date: Jan. 23, 1981
§ 102(e) Date: Jan. 23, 1981

[87] PCT Pub. No.: WO80/02594
PCT Pub. Date: Nov. 27, 1980

[30] Foreign Application Priority Data

May 24, 1979 [GB] United Kingdom ............... 7918101

[51] Int. Cl.³ .......................................... G01N 29/00
[52] U.S. Cl. .................................. 73/606; 73/644
[58] Field of Search ............... 73/618, 619, 606, 644

[56] References Cited

U.S. PATENT DOCUMENTS 3,832,888  9/1974  Langlois ........................... 73/605
4,028,933  6/1977  Lenvars et al. .................... 73/627

FOREIGN PATENT DOCUMENTS 1575273  9/1980  United Kingdom ............... 73/644

OTHER PUBLICATIONS

"The Acoustic Microscope", Quate, *Scientific American*, Oct. 1979, vol. 241, No. 4, pp. 62-70.

Primary Examiner—Howard A. Birmiel
Attorney, Agent, or Firm—Cushman, Darby & Cushman

[57] ABSTRACT

A scanning acoustic microscope comprises transducer means (10, 12, 14) to provide a convergent beam of acoustic radiation; means (20, 22) to cause relative movement in the focal plane of the focus of the beam and a sample (16); transducer means (10, 12, 14) to receive acoustic radiation modulated by the sample near the beam focus; and means (30) to supply a pressurized gas to a volume surrounding the transducer means and the sample.

12 Claims, 4 Drawing Figures

SCANNING ACOUSTIC MICROSCOPE

It is known that an image of a sample can be provided by causing a focussed beam of high frequency acoustic radiation to scan across the sample surface, and converting the transmitted or reflected acoustic radiation into an optical signal. The sample is coupled to a suitable transducer by a liquid, such as water, liquid helium or liquid argon. In such a system, there are very large signal losses, mainly in the coupling liquid which has a high absorption coefficient. For typical liquids the absorption coefficient is proportional to the square of the frequency up to and beyond 10 GHz, and the acoustic wavelength varies inversely as the frequency. It can be shown that the resolution of a scanning acoustic microscope is about ⅜ of the acoustic wavelength in the coupling medium.

Suppose the transit time and loss through the coupling fluid are fixed at T sec and N nepers respectively. Further suppose that the fluid path length is L and the attenuation coefficient is $\alpha$ at a frequency f.

If $X = \alpha/f^2$ then $N = Xf^2L$ therefore $f^2 = N/XL$      [1]

If V is acoustic velocity and $\lambda$ is acoustic wavelength, then $V = f\lambda$. Substituting in equation [1].

$\lambda = V/f = V(L/N)^{\frac{1}{2}}(X)^{\frac{1}{2}}$

But $L = VT$ therefore $$\lambda = (V)^{3/2} \left(\frac{T}{N}\right)^{\frac{1}{2}} (X)^{\frac{1}{2}} \quad [2]$$

$= \kappa(V)^{3/2} (X)^{\frac{1}{2}}$ and resolution $\simeq \frac{3}{8} k(V)^{3/2}(X)^{\frac{1}{2}}$ where k is a constant. Therefore for a fixed loss and transit time in the coupling medium, the theoretically attainable resolution is proportional to the product of (the acoustic velocity in liquid)$^{3/2}$ and the square root of a constant of the liquid.

It is also known that in a gas at atmospheric pressure, while the acoustic velocity is typically 5 to 10 times lower than in liquids, thus increasing resolution, values of X are typically 100 to 1000 times higher than in water which offsets the gain in resolution as indicated by equation [2]; use of a gas as a coupling medium in a scanning acoustic mircoscope therefore did not seem practical because predicted resolution was lower than for a liquid-coupled system.

However, we now believe that use of a gas may, under certain conditions, be advantageous.

According to the invention, a scanning acoustic microscope comprises transducer means to provide a convergent beam of acoustic radiation; means to cause relative movement in the focal plane of the focus of said beam and a sample under investigation; transducer means to receive acoustic radiation modulated by the sample near the beam focus; and means to supply a pressurised gas to a volume surrounding the transducer means and the sample.

Preferably the gas is at a pressure of at least 10 atmospheres, and usually a pressure of at least 100 atmospheres will be required. The gas may be a monatomic gas such as argon or xenon.

When the microscope is used in a transmission mode, a transmitting transducer will provide the convergent beam and a separate receiving transducer will sense the modulated radiation. When the microscope is used in a reflection mode, a single transmitting/receiving transducer can be used.

A microscope according to the invention can be used in any of the conventional modes. Phase and amplitude information can be provided, pulsed or continuous wave operation is possible, and dark field imaging may be used.

The present invention is based on the discovery, theoretically predicted by the inventor, that for a monoactomic gas at a pressure of about 100 atmospheres, the constant X is of the same order as its value for liquids. This discovery, in conjunction with the classical equation showing that velocity of sound in a gas is independent of pressure, finds practical application for the first time in a novel and inventive scanning acoustic microscope in which a pressurised gas is used as a coupling medium. It is believed that this is the first time that the effect of gas pressure on absorption of sound in a gas has been considered either theoretically or practically in acoustic microscopy.

In classical gas theory considering behaviour of an ideal gas, two absorption mechanisms are applicable to explain absorption of sound by the gas, i.e. viscous damping, and heat conduction caused by direct transfer of atomic momentum. These two effects are about the same order of magnitude for argon and xenon.

Considering acoustic absorption $\alpha$ due to viscous damping and thermal conduction, the classical expression is $$\alpha = \frac{2\pi^2 f^2}{\rho V^3}\left[\frac{4}{3}\eta + (\gamma - 1)\frac{K}{Cp}\right] \quad [3]$$

where $\eta$ is shear viscosity, $\rho$ is density, $\gamma$ is the ratio of molar heat capacities, Cp is the specific heat at constant pressure and K is the thermal conductivity. The first term within square brackets corresponds to viscous damping and the second term to thermal conduction loss. As before, f is frequency and V is acoustic velocity.

Also $V = (\gamma P/\rho)^{\frac{1}{2}}$      [4]

where P is gas pressure and $\gamma$ is the ratio of the molar heat capacities. Substituting for V in equation [3]:

$$\frac{\alpha}{f^2} = X = \frac{2\pi^2}{\gamma PV}\left[\frac{4}{3}\eta + (\gamma - 1)\frac{K}{Cp}\right] \quad [5]$$

But $V = (\gamma P/\rho)^{\frac{1}{2}} = (\gamma RT/M)^{\frac{1}{2}}$      [6]

where R is the gas constant, T the absolute temperature and M the molecular weight of the gas. Substituting for V in equation [5]:

$$\frac{\alpha}{f^2} = (2\pi^2)\frac{1}{\gamma P}\left(\frac{M}{\gamma RT}\right)^{\frac{1}{2}}\left[\frac{4}{3}\eta + (\gamma - 1)\frac{K}{Cp}\right] \quad [7]$$

The kinetic theory of gases predicts that $\eta$, $\gamma$, K and Cp are independent of pressure. Argon is a good approximation to an ideal gas and the shear viscosity of argon varies by less than 10% for pressures between 1 and 100 atmospheres. Also the quantity $(\gamma-1)K/Cp$ is nearly constant over this range. Under these conditions, equation [7] predicts that the value of $X=\alpha/f^2$ in argon is inversely proportional to gas pressure P at a fixed temperature T. Also, equation [6] shows that the acoustic velocity in argon is solely a function of temperature and is independent of pressure. Thus it is predicted that an increase in gas pressure P decreases the absorption coefficient $\alpha/f^2$ while velocity V remains constant.

In practice, the acoustic absorption in the gas and the acoustic velocity will also be governed by any relaxation processes which occur within the gas molecule. However, if a monatomic gas is used, there will be no such process.

It can therefore be predicted that in a scanning acoustic microscope, the resolution is theoretically greater by a factor of 5 when the coupling medium is argon gas at 250 atmospheres pressure or by a factor of 4 for xenon gas at 40 atmospheres pressure in comparison with a water-coupled microscope.

An improved scanning acoustic microscope will be described with reference to the accompanying drawings in which.

Figure 1:
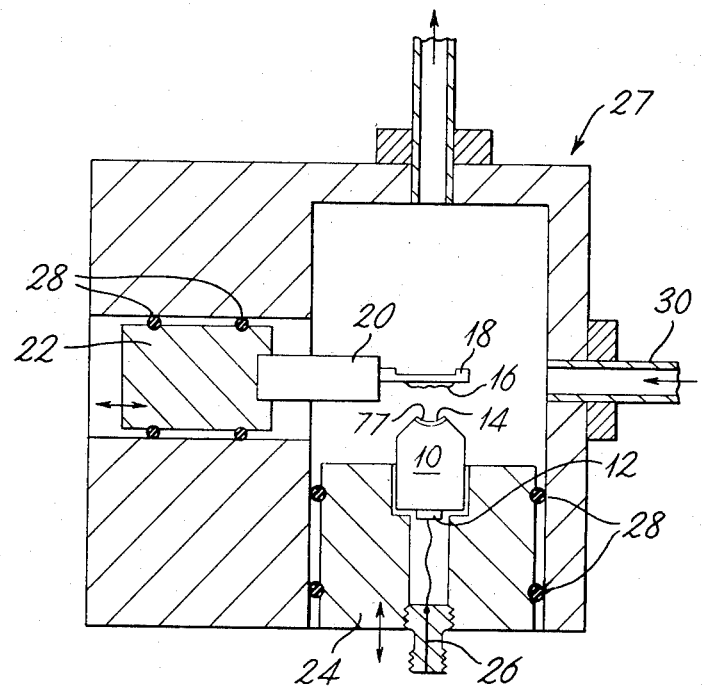
FIG. 1 is a section through a microscope according to the invention.

FIG. 1 shows a scanning acoustic microscope operable in a reflection mode. An acoustic transmitter/receiver 10, consisting of a rod-shaped sapphire crystal, has at one end a flat face to which is attached a piezoelectric transducer and electrode 12 and at the opposite end a concave face 14. If an alternating electric signal for example at 3 GHz is applied to the electrode 12, an acoustic wave is generated which passes through the concave face 14 which causes the beam to converge to a focus. In the focal plane lies a specimen 16 attached to a specimen holder 18. The holder 18 is supported by a piezoelectric bimorph 20 arranged so that excitation of the bimorph causes the specimen holder to be scanned normally to the plane of the drawing. The bimorph 20 is supported by a first movable carrier 22 which can be driven as indicated by the arrow to scan the specimen holder in the plane of the figure. The two scanning movements together allow relative movement of the focus of the acoustic beam and the specimen in two dimensions; the movements are linked to provide a raster scan. Acoustic radiation reflected by the specimen in the region of the focus is received by the transmitter/receiver 10, and an alternating electric signal from electrode 12 passes to suitable detection equipment.

The transmitter/receiver 10 is supported by a second movable carrier 24 movement of which alters the position of the focal plane relative to the specimen 16. The carrier 24 has a central aperture through which passes the electrical connection 26 to the electrode 12. The carriers 22, 24 are movable within apertures in the walls of a gas-tight pressure chamber 27 and a gas tight seal is provided by "O" rings 28. Gas can be supplied through a supply pipe 30 to the chamber 27; the gas surrounds the concave end 14 of the transmitter/receiver and the sample 16 so as to act as a coupling medium for acoustic radiation.

Figure 2:
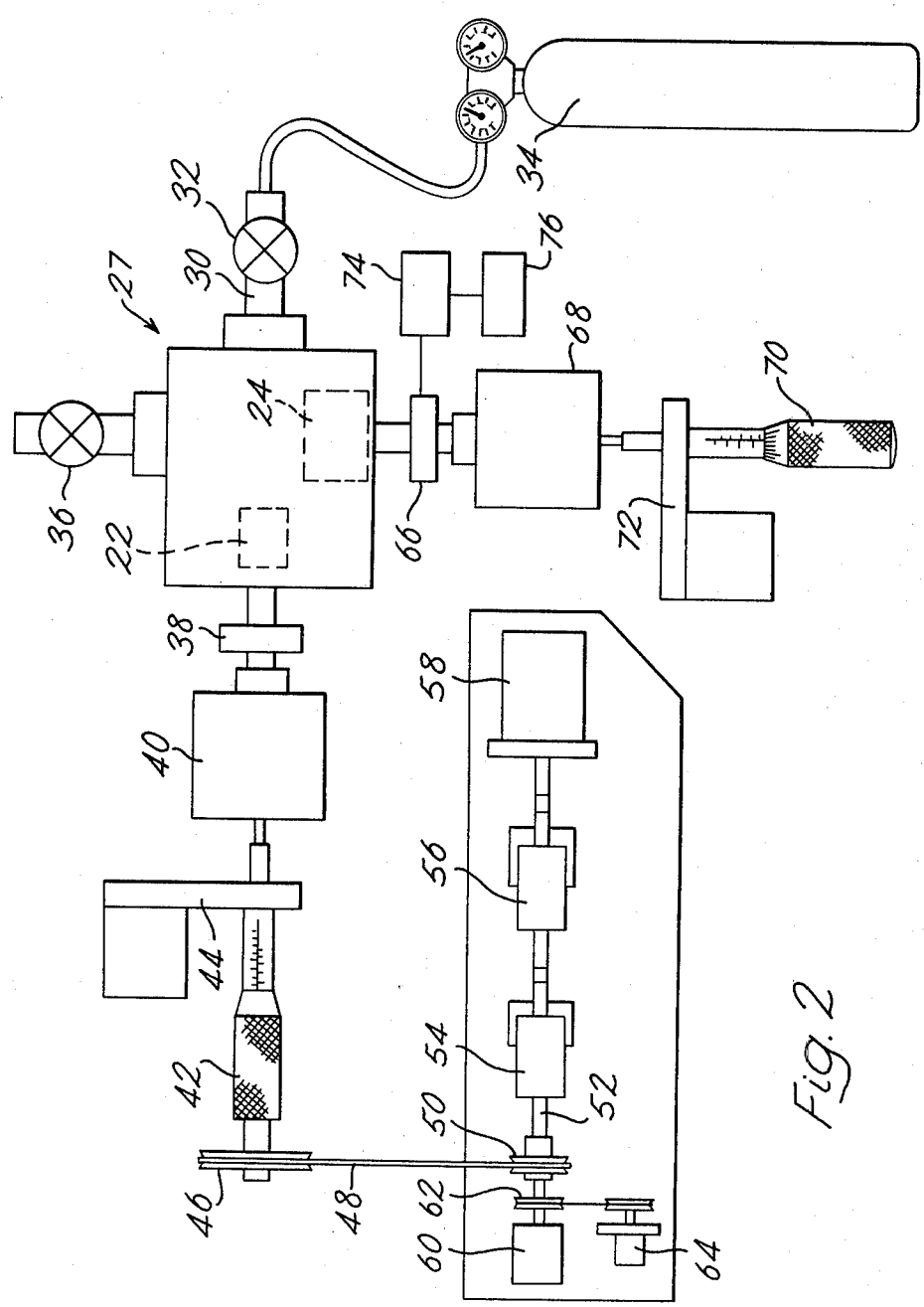
FIG. 2 is a plan view of the microscope of FIG. 1 and its associated control system.

In FIG. 2, the chamber 27 is shown connected through pipe 30 and a control valve 32 to a supply 34 of pressurised gas; typically argon or xenon at 40 atmospheres is supplied. The chamber 27 also has an exhaust valve 36.

The first carrier 22 within the chamber is driven to give the scanning movement in the plane of the figure via a guide 38 and hydraulic link 40 by a micrometer 42 held in a support 44. The micrometer 42 is itself driven through a large diameter pulley wheel 46 connected by a band 48 to a small pulley wheel 50 carried by an axle 52 driven through two gear boxes 54, 56 by a d.c. motor 58. The axle 52 is carried by a bearing 60 and itself carries a pulley 62 connected to a potentiometer 64.

The reduction provided by the gears 54, 56 and the ratio of pulleys 46, 50, allows the micrometer 42 to advance the carrier 22 at a required speed. The hydraulic link 40 is used to reduce the force on the micrometer threads. The potentiometer 64 provides an electrical output corresponding to the position of the carrier 22.

The position of the focal plane is controlled by movement of the carrier 24 within the chamber. The carrier 24 is driven via a guide 66 and hydraulic link 68 by a micrometer 70 held in a support 72. The position of the focal plane is indicated by direct reading of the micrometer.

The transmitter/receiver, not shown in FIG. 2, is connected to conventional scanning acoustic microscope electronic circuitry 74 providing an exciting signal and signal decoding facilities which supply a signal to a visual display unit 76.

While the theoretical resolution of the acoustic microscope has already been discussed, one further problem is the large reflection loss at the curved interface 14 of the transmitter/receiver 14 and the coupling gas. When the interface is sapphire and the coupling gas is argon at atmospheric pressure, the reflection loss is 42 decibels. Application of a quarter-wave impedance matching layer of polyethylene 77 reduces the loss to 14 decibels. Moreover, the impedance match improves with increase in gas pressure, and at 130 atmospheres the quarter-wave layer provides a theoretically perfect match. Such a technique would be viable for frequencies up to 500 MHz. However at higher frequencies, the attenuation in polyethylene is too large. One could then use two or three quarter wave layers of different material to form a multiple matching layer. For example, when the interface is sapphire, and the coupling gas is argon at 250 atmospheres, a quarter wave matching layer combination of aluminium/platinum/aluminium results in a reflection loss of 1.3 dB. Alternatively if the interface is fused quartz, a quarter wave matching layer combination of platinum/aluminium results in a reflection loss of 3.2 dB (at 250 atm).

Figure 3:
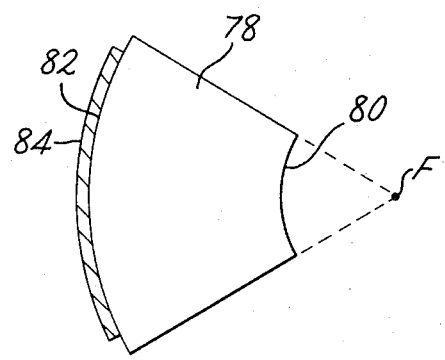
FIG. 3 is a schematic section through an acoustic transducer suitable for use in the microscope and FIG. 4 is a section through an alternative embodiment of a microscope according to the invention.

An alternative method of reducing reflection loss is shown in FIG. 3. A transmitter/receiver comprises a sapphire crystal 78 of conical form with a concave face 80 at the cone apex and a convex face 82 at the opposite end, the faces being confocal at F. A piezoelectric transducer and electrode layer 84, such as a thin film of zinc oxide, is applied to the convex face. The whole transmitter/receiver acts as a confocal resonator, and there is a good impedance match with a gaseous medium in contact with concave face 80. However, with such a transmitter/receiver, the microscope can operate only in a continuous wave mode.

Figure 4:
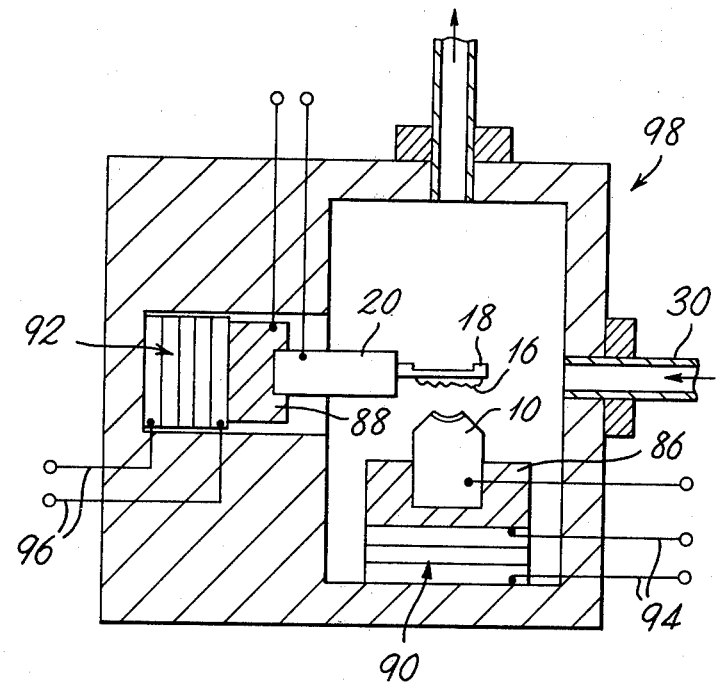

The scanning acoustic microscope illustrated in FIGS. 1 and 2 is capable of working at pressures up to about 40 atmospheres. At higher pressures, the forces on the piston-like carriers and on the "O" rings would be too high. An alternative embodiment suitable for use at 250 atmospheres pressure is shown in FIG. 4. Parts identical to those in FIG. 1 are given the same reference numerals. The transmitter/receiver 10 and the bimorph 20 are supported by respective holders 86, 88 each connected to a piezoelectric scanner 90, 92 by supply leads 94, 96. The piezoelectric scanner 92 supplies the scanning movement in the plane of the diagram and the scanner 90 provides focus adjustment. The chamber 98 can be sealed using only static packed seals (not illustrated).

It is an advantage of a scanning acoustic microscope according to the invention that it can be used to study living organisms at sub optical resolution; at present, such high resolution can only be obtained by use of a cryogenic liquid as a coupling medium, so that it is impossible to study living material. Living systems are extremely sensitive to temperature but are quite insensitive to pressure variations. The ability to work at room temperature thereby avoiding temperature stresses in, for example, microelectronic specimens will also serve to extend the capability of high resolution acoustic microscopy.

I claim:

1. A scanning acoustic mircoscope comprising:
   transducer means for providing a convergent beam of acoustic radiation;
   means for causing relative movement in the focal plane of the focus of said beam and a sample under investigation;
   transducer means for receiving acoustic radiation modulated by the sample near the beam focus; and
   means for supplying a gas at higher than atmospheric pressure to a volume between surrounding the transducer means and the sample.

2. A scanning acoustic microscope according to claim 1 in which the gas is at a pressure of at least 10 atmospheres.

3. A scanning acoustic microscope according to claim 1 or claim 2 in which the gas is a monatomic gas.

4. A scanning acoustic microscope according to claim 3 in which the gas is argon or xenon.

5. A scanning acoustic microscope according to claim 1 and operable in a reflection mode in which a transmitting/receiving transducer (10) both provides a convergent beam of acoustic radiation and senses acoustic radiation modulated by the sample near the beam focus.

6. A scanning acoustic microscope according to claim 5 in which the transmitting/receiving transducer (10) comprises a rod-shaped crystal having at one end a flat face which carries a piezoelectric transducer (12) and at the other end a concave face (14) which carries an impedance matching layer (77).

7. A scanning acoustic microscope according to claim 6 comprising a sapphire crystal (10) carrying on its concave face (14) an impedance matching layer (77) consisting of a quarter-wave layer of polythylene, the gas being argon at 130 atmospheres pressure.

8. A scanning acoustic microscope according to claim 6 comprising a sapphire crystal (10) carrying on its concave face (14) an impedance matching layer (77) consisting of successive quarter-wave layers of aluminium, platinum and aluminium, the gas being argon at 250 atmospheres.

9. A scanning acoustic microscope according to claim 6 comprising a quartz crystal (10) carrying on its concave face (14) an impedance matching layer (77) consisting of a quarter-wave layer of platinum and a quarter-wave layer of aluminium.

10. A scanning acoustic microscope according to claim 5 in which the transmitting/receiving transducer comprises a crystal (78) of conical form having a concave face (80) at the cone apex and a convex face (82) at the opposite end, the faces being confocal, and a piezoelectric transducer (84) in contact with the convex face.

11. A scanning acoustic mircoscope system comprising a scanning acoustic microscope according to claim 1 and further comprising circuit means (74, 76) for providing an exciting signal to the transducer means which provides a convergent beam of acoustic radiation, for receiving an information signal from the transducer means which senses acoustic radiation modulated by the sample near the beam focus, for decoding the information signal, and for supplying a signal to a visual display unit; and means (66, 68, 70) for causing relative movement between the focal plane and the sample in a direction transverse to the focal plane.

12. A scanning acoustic microscope according to any one of claims 1 through 11 in which the pressurised gas is an approximately ideal gas.

* * * * *